United States Patent [19]

Prashad

[11] Patent Number: 5,068,175

[45] Date of Patent: Nov. 26, 1991

[54] METHOD OF DETECTING RAS ONCOGENE RELATED MALIGNANCIES

[75] Inventor: Nagindra Prashad, Houston, Tex.

[73] Assignee: Board of Regents, The University of Texas Sysem, Austin, Tex.

[21] Appl. No.: 358,449

[22] Filed: May 26, 1989

[51] Int. Cl.$^5$ .................... C12Q 1/68; C07H 15/12; C12N 15/00; G01N 33/48

[52] U.S. Cl. ........................................ 435/6; 536/27; 935/77; 935/78; 530/406; 436/64; 436/813

[58] Field of Search ................. 435/6; 536/27; 935/77, 935/78; 530/406; 436/813, 64

[56] References Cited

U.S. PATENT DOCUMENTS

| | | | |
|---|---|---|---|
| 4,699,877 | 10/1987 | Cline et al. | 435/6 |
| 4,963,658 | 10/1990 | Kurg et al. | 530/406 |

OTHER PUBLICATIONS

Maniatis et al., Molecular Cloning–A Laboratory Manual, 1982, Cold Spring Harbor Laboratory, p. 151.

Ashii et al., Science, vol. 232, pp. 1410–1413 (1986).

C. J. Der et al., "Altered gene products are associated with activation of cellular ras genes in human lung and colon carcinomas," Cell 32:201–08 (1983).

L. A. Feig et al., "Somatic activation of ras gene in human ovarian carcinoma," Science 223:698–700 (1984).

M. S. McCoy et al., "Characterization of a human colon/lung carcinoma oncogene," Nature 302:79–81 (1983).

M. V. Viola et al., "Expression of ras oncogene p21 in prostate cancer," New Eng. J. of Med. 314:133–137 (1986).

S. Ishii et al., "Binding of the Spl transcription factor by the human Harvey rasl proto–oncogene promoter," Science 232:1410–1413 (1986).

H. Dosaka et al., "Immunohistochemical analysis of human lung cancers with anti–ras p21 monoclonal antibodies," Int. J. Biol. Markers 2(2):75–82 (1987).

P. Garrett et al., "Clinical utility of oncofetal proteins and hormones as tumor markers," Medical Clinics of N. Am. 70(b):1295–1306 (1986).

B. Czerniak et al., "ras oncogene p21 as a tumor marker in the cytodiagnosis of gastric and colonic carcinomas," Cancer 60:2432–2436 (1987).

L. M. Stock et al., "ras related oncogene protein as a tumor marker in transitional cell carcinoma of the bladder," J. of Urol. 137(4):789–792 (1987).

H. Honkawa et al., "Identification of the principal promoter sequence of the C–H-ras transforming oncogene: deletional analysis of the 5′-flanking region by focus formation," Mol. Cell. Biol. 7(8):2933–2940 (1987).

(List continued on next page.)

Primary Examiner—Christine Nucker
Assistant Examiner—Mindy B. Fleisher
Attorney, Agent, or Firm—Arnold, White & Durkee

[57] ABSTRACT

Methods and composition for detecting the presence of human ras oncogene related malignancies are provided, where a biological sample is assayed for protein(s) specific to a DNA sequence. In the methods of this invention, the test reaction involves admixing a biological sample from cancer patients or control donors with labelled ras oncogene promoter DNA. The admixture is incubated under conditions favorable for promoting specific interactions between proteins and the labelled DNA. Thereafter, the admixture is separated by charge and size in an electrophoretic field and the protein-DNA interactions are identified depending on the method of label employed. Bands migrating at a slower rate than the uncomplexed DNA are indicative of a protein-DNA interaction (i.e. circulating serum protein(s) from cancer patients interacting specifically with a region(s) of the ras oncogene promoter DNA). Utilizing this experimental protocol, the serum proteins of interest include at least four different proteins that specifically interact with a region or regions of the ras oncogene promoter DNA. The four different factors, ranging in molecular weight from about 200 Kd to about 50 Kd are proteinaceous in nature as demonstrated by their trypsin sensitivity and heat stability.

16 Claims, 4 Drawing Sheets

OTHER PUBLICATIONS

M. G. Borrello et al., "Modulation of the human Harvey-ras oncogene expression by DNA methylation," Oncogene Res. 2(2):197–203 (1988).

S. Ishii et al., "Promoter region of the human Harvey ras proto-oncogene: Similarity to the EGF receptor proto-oncogene promoter," Science 230(4732):1378–1381 (1985).

G. E. Gallick et al., "Expression of p21 ras in fresh primary and mestastic human colorectal tumors," Proc. Natl. Acad. Sci. 82:1795–1799 (1985).

J. L. Bos et al., "Prevalence of ras gene mutations in human colorectal cancers," Nature 327:293–297 (1987).

```
Nae I     Xho I    •200                •                •                •
(116)---CTCGAGCAACCCCGAGCTCGGCTCCGGTCTCCAGCCAAGCCCAACCC

•                •       I        •                •            • II         •
CGAGAGGCCGCGGCCCTACTGGCTCCGCCTCCCGCGTTGCTCCCGGAAGCCCCGCCCGAC

•310         •                •                •    III     •  ┌─ApaI
CGCGGCTCCTGACAGACGGGCCGCTCAGCCAACCGGGGTGGGGCGGGGCCCGATGGCGCG

•400 IV         •
 ┌─────────┐
 │CAGCCAAT│GGTAGGCCGCGCCTGGCAGACGGACGGGCGCGGGGCGGGGCGTGCGCAGGCC
 └─────────┘
       ┌─HintI
       •         •                •                •                •
CGCCCGAGTCTCCGCCGCCCGTGCCCTGCGCCCGCAACCCGAGCCGCACCCGCCGCGGAC

•       •500     •    V      •    VI     •                 ↓    •
GGAGCCCATGCGCGGGGCGAACCGCGCGCCCCCGCCCCCGCCCCGCCCCGGCCTCGGCCC

↓ •    ↓     • ↓       •             Splice    Nae I
CGGCCCTGGCCCCGGGGGCAGTCGCGCCTGTGAACGGT---(666)
```

METHOD OF DETECTING RAS ONCOGENE RELATED MALIGNANCIES

BACKGROUND OF THE INVENTION

The present invention relates to molecular reagents and molecular diagnostic tests useful for detecting certain proteins produced by tumors.

Proteins that are specifically associated with certain tumors have been described as early as 1965. These tumor associated proteins or tumor markers would be a powerful tool in detecting certain malignancies if they were qualitative. Most of the currently identified tumor markers are quantitative instead of qualitative. Garrett and Kurtz (*Medical Clinics of North America*, 70:1295-1306 (1986)) defined the ideal biological tumor marker as one that is a) specific without false-positive results, b) sensitive without false-negative results and c) capable of demonstrating an absolute correlation with the extent of disease. To date, for a variety of reasons, unique and specific tumor markers have not been adequately characterized. The broad classification of tumor markers can be divided into two groups: (1) tumor associated proteins and (2) oncogene products.

A wide variety of tumor associated proteins found in certain tumor tissues and serum have been described. They include carcinoembryonic antigen (CEA), tumor associated glycoprotein (TAG), CA19-9, human chorionic gonadotropin (HCG), alpha-feto protein (AFP), and a 145,000 nucleolar protein (p145) (Schlom, J. Cancer Research 46:3225-3238 (1986); Chan, J. C., Cancer Bulletin 40:213-217 (1988); Freeman, J. W., et al, Cancer Research 46:3593-3598 (1986); Gion, M., et al, International Journal of Biological Markers, 1:33-38 (1986)). All of these proteins are associated with a wide range of human malignancies.

Oncogene products are a second category of tumor markers found in human tumors. Proto-oncogenes are normal cellular genes which are involved in normal growth and differentiation. These proto-oncogenes can transform into oncogenes by one of the following mechanisms: point mutations in the coding region, amplification of genes, or chromosomal translocation. Once a proto-oncogene is changed into an oncogene, neoplastic growth occurs. The ras and myc families of cellular oncogenes are two of the most frequently identified activated oncogenes. The ras family of oncogenes consist of the Harvey ras, Kirsten ras and neuroblastoma ras oncogene. Activation of ras oncogene causes an increase of ras specific protein (p21) in colon, colorectal, lung, mammary, neuroblastoma, prostate, ovarian, melanoma and bladder carcinomas (Der, C. J. and Cooper, G. M., Cell 32:201-208 (1983); Feig, L. A., et al, Science 223:698-700 (1984); McCoy, M. S., et al, Nature 302:79-81 (1983); Viola, M. V., et al. New England Journal of Medicine 314:133-137 (1986). Thus, one can readily deduce that the p21 ras oncogene protein is a powerful tumor marker.

In higher eukaryotic cells, the regulation of gene expression is often mediated by turning on and off RNA synthesis in a temporally ordered manner. A popular hypothesis for the synthesis of messenger RNA by RNA polymerase II, involves specific promoter interaction with one or more cellular transcriptional factors. To be effective, these transcriptional factors must recognize and bind to specific DNA sequences located within the promoter region of the eukaryotic gene of interest. Most researchers believe that both temporal regulation and tissue specificity of transcription are controlled by these cellular DNA binding proteins (Dynan, W. S. and Tijian, R., Cell 35:79-87 (1983)). For accurate and optimal initiation of transcription, the structural organization of different promoters recognized by polymerase II involve multiple common elements located upstream of the RNA start site. Specific DNA sequences for the promoter region of a gene (consensus sequences) are recognized by a limited number of nuclear proteins. A variety of nuclear proteins (SPI, NFI, API and COUP) have been shown to specifically recognize and interact with certain promoter sequences.

Since oncogene products belong to a broad classification of tumor markers, the identification of a tumor marker protein which specifically bound to a region of the human Harvey ras promoter would be very useful and powerful. Any tumor markers identified in this manner may be transcriptional activators of the Harvey ras oncogene. Since the p21 Harvey ras protein product is found in a variety of human malignancies (colon, colorectal, lung, mammary, neuroblastoma, prostate, ovarian, melanoma and bladder), identifying a transcriptional activator of the Harvey ras oncogene would be most beneficial.

There remains a profound need for an improved method of identifying human malignancies at an early stage. The present invention provides a reliable, sensitive, specific, efficient and reproducible method for the detection of circulating serum tumor markers (factors) specific to the ras oncogene promoter.

SUMMARY OF THE INVENTION

The present invention identifies and characterizes specific circulating serum factor(s) as a tumor associated marker protein and provides a method for its use to detect the presence of ras oncogene family related malignancies.

The circulating serum factor(s) presented in this invention are identified as those proteins capable of binding specifically to a region(s) of a ras oncogene promoter DNA sequence. These serum factors specific for the oncogene promoter DNA are predominantly found in patients with ras oncogene family related malignancies. No serum factor specific for the ras oncogene promoter DNA sequence (above background levels) is detected in control, tumor-free donors.

The proteins which specifically bind to the ras promoter DNA may be transcriptional activators and thus may play a role in modulating the expression of the Harvey ras oncogene. These serum factors are trypsin sensitive and heat stable. To date four human serum proteins specific for the human ras oncogene promoter DNA have been identified and range in molecular weight from about 200 Kd to 50 Kd (about 170 Kd, 75 Kd, 70 Kd, 55 Kd).

The present invention involves a method for identifying and characterizing specific factors as a tumor associated marker and provides a method for their use in detecting the presence of ras family promoter oncogene related malignancies. This method includes: collecting a biological sample from a human subject; incubating the biological sample with a labelled ras oncogene promoter under conditions effective to promote interactions between factors from the biological sample and specific segments of the ras oncogene promoter; separating a factor-DNA complex according to an electrophoretic migration mobility rate in a gel matrix; and visualizing the labelled factor-DNA complex by observing bands migrating at a slower rate as compared to the free DNA, thereby detecting a ras family related malignancy by identifying the presence of the specific factor-DNA complex.

In terms of collecting a biological sample from a human subject, the human subject includes patients with a ras family related malignancy, patients with a ras family unrelated malignancy or normal control tumor free donors. The ras oncogene family related malignancies encompass a number of reported malignancies, including breast, colon, prostate cancer and melanoma, which express the ras oncogene protein products. The ras oncogene family includes Harvey, Kirsten and neuroblastoma ras related malignancies. The ras unrelated malignancies include a number of cancers which have been reported to produce other oncogene protein products (i.e. myc-, fos- and abl-oncogenes). This category of patients would include those individuals with leukemia, brain and bone cancer.

In terms of the biological sample, the source may be blood components, urine, cerebro-spinal fluid, lung lavage, ascites fluid, saliva or tissue biopsy samples. The blood components which would be suitable for these assays include serum, plasma, or white blood cells. The tissue biopsy samples may be obtained from either normal tumor free control donors, patients with ras related malignancies or from patients with other oncogene related malignancies. Although all the above described biological samples are suitable for the assays, blood serum or plasma yielded the optimum results in terms of specificity between the protein-DNA interaction.

The labelled oncogene promoter is isolated from one of the ras oncogene family members. The ras oncogene family is defined to include the Harvey, Kirsten or neuroblastoma ras oncogenes. As used herein, promoter is defined as the region of DNA located 5' to the transcriptional start site which contains the necessary components to initiate transcription. The ras promoter DNA described herein is isolated from the ras oncogene, employing standard technology known to a person skilled in the art, for example by using Nae-1 restriction enzyme. This Nae 1-Nae 1 restriction fragment comprises 551 base pairs of the ras oncogene promoter region encompassing base pairs 116 to 666. This 551 base pair promoter region may be used alone as a fragment, or it can either be linked to the entire ras DNA sequence or a portion thereof or to a heterologous eukaryotic or prokaryotic DNA sequence (a partial or whole gene). In terms of the ras oncogene, any promoter region from one of the three family members would be suitable for these experiments. The promoter sequence does not encode a protein structure as it only comprises the promoter region of the oncogene.

The above described ras oncogene sequence which is used in the mobility band shift assay is labelled to identify the complexed DNA from the uncomplexed DNA. The ras oncogene sequence may be labelled by a variety of known techniques familiar to those skilled in the art. The labels that are commonly employed to tag DNA are radioactivity, enzymes, colorometric markers, fluorometric markers, luminescent markers or biotin. Labelling the DNA with radioactivity is routinely employed because the free labelled DNA is relatively easily separated from the labelled protein-DNA complex and therefore is the method of choice used herein.

The protein-DNA complex is formed under the conditions established in the embodiments disclosed herein. These conditions are effective to promote interactions between proteins and certain regions of the ras oncogene promoter DNA thus allowing the formation of a protein-DNA complex. In terms of this disclosure, factor-DNA complex and protein-DNA complex are used interchangeably and are defined to include the interaction between a factor or protein from the biological sample and the labelled ras oncogene promoter DNA sequence. This protein-DNA complex is further separated in an electrophoretic field. The matrix composition of the electrophoretic field may be composed of acrylamide or agarose. Either of these two matrixes separate on the basis of charge and size. For the purposes disclosed herein, optimum results are obtained when acrylamide gel matrixes are employed.

The protein-DNA complex was further analyzed for heat stability and trypsin sensitivity. Trypsin sensitivity and heat stability are two methods commonly used to characterize specific factors as proteins. The techniques employed to characterize these factors are standard, routinely employed and are known to those skilled in the art. Briefly, these techniques involve incubating the factor in question with trypsin or heating the factor to 55° C. for at least 30 minutes. As reported in the literature, trypsin sensitivity and heat stability are two characteristics which define a proteinaceous substance. In terms of this disclosure, protein and proteinaceous are used interchangeably and are intended to have the same definition.

To characterize the protein-DNA complex, the proteins are eluted from the mobility band shift acrylamide gel and are further separated on another acrylamide gel. The proteins are visualized by one of the available staining techniques commonly known to those familiar in the art. Although there are a variety of staining techniques, one method of choice employs silver staining the proteins and comparing their molecular weights to the molecular weights of known standard proteins. The molecular weights of the proteins in question are determined by using migration rates of the standard proteins of known molecular weights. This procedure is known to those skilled in the art and is routinely employed.

The proteins which are involved in the protein-DNA complex can be used to generate antibodies. The techniques which can be employed to generate polyclonal or monoclonal antibodies specific to one protein, are familiar to those skilled in the art of producing antibodies. It is with one of these routine procedures that antibodies will be produced against each one of the proteins that specifically interact with certain regions of the ras oncogene promoter.

Assembling a diagnostic kit comprising multiple containers consisting of the following components involve standard protocols which are known to those skilled in the art. The components of this diagnostic kit include: labelled ras oncogene promoter DNA, a positive and negative control protein and instructions to direct the user in separating and identifying the protein-labelled DNA complex indicative of an oncogene related malignancy. The ras oncogene promoter DNA can be labelled by one of the available methods known to those skilled in the art and which were described supra. The positive control protein would be comprised of one of the four proteins known to specifically interact with a region or regions of the ras oncogene promoter DNA sequence. The negative control protein would comprise a ras irrelevant protein which does not interact with the labelled ras oncogene promoter DNA sequence.

Assembling a diagnostic kit comprising multiple containers consisting of the following involve standard protocols which are known to those familiar and skilled in the related art. The components of this diagnostic kit include: one or more primary antibodies specific to one of the proteins which interact with a region or regions of the ras oncogene promoter DNA sequence, one or more secondary antibodies which specifically interact with the primary antibody, a labelled tag for identifying the secondary antibody, a positive and negative control antigen and instructions to direct the user in separating and identifying the antibody-protein complex indicative of an oncogene related malignancy. The antigen which serves as the positive control may be one of the four proteins known to specifically interact with a region or regions of the ras oncogene promoter DNA sequence. The methodology employed to identify the antibody-antigen (protein) complex may be one of the available protocols known to those skilled in the art which involve detection of an antibody-antigen (protein) complex. Examples of such assays include Western blot, immunodot blot, enzyme immunoassay or radioimmunoassay. Any of the above described methods are suitable for defining or identifying the antibody-antigen (protein) complex.

Synthetic oligomers can be generated and further employed to identify oncogene related malignancies, once specific regions or sequences from oncogene promoters are identified. The technologies employed to identify and generate the synthetic oligomers are known to those skilled in the art. Standard protocols used for identifying certain regions which are involved in protein-DNA interactions include footprinting and sequencing the areas involved.

DETAILED DESCRIPTION OF PREFERRED EMBODIMENTS

The following discussion is in terms of the preferred embodiments of this invention, which represent the best mode known to Applicant at the time of this application.

Serum Factors from Cancer Patients and Normal Donors

In accordance with this invention, the discovery that certain serum factors from cancer patients bind specifically to ras oncogene promoter DNA is of particular value in a diagnostic screening method for early detection of ras oncogene related malignancies. The serum factors of this invention consist of certain proteins that specifically interact with a region or regions of the ras oncogene promoter DNA.

Sera from cancer patients were obtained from Dr. Sanford Stass, Department of Laboratory Medicine, M.D. Anderson Cancer Center.

As used within the context of this invention, the serum proteins of interest include at least the four different proteins that specifically interact with a region or regions of the ras oncogene promoter DNA. The four different factors ranging in molecular weight from about 200 Kd to about 50 Kd are proteinaceous in nature as demonstrated by their trypsin sensitivity and heat stability.

Also used within the context of this invention, serum and serum factors obtained from normal donors were processed and handled in the same manner as the sera obtained from the cancer patients. The above-mentioned four serum proteins were not detected in the sera from normal donors or were at least 30-fold less than the cancer patients.

Ras Oncogene Promoter DNA Probe

Figure 1:
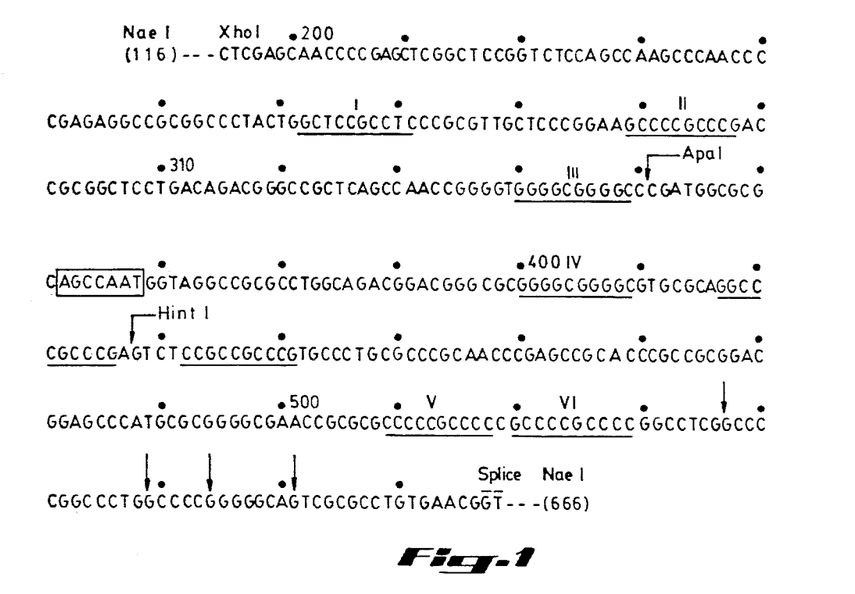
FIG. 1: Nucleotide sequence of the human Harvey ras promoter region. The major transcriptional start sites (large arrows) and the splice site are shown. The Nae 1Nae 1 DNA fragment extends 551 base pairs from 116–666 (Ishii, S., et al, Science 232:1410–1413 (1986)).

Further in accordance with this invention, ras oncogene promoter deoxyribonucleic acid (DNA) was isolated, purified and radiolabelled for use as an interactive material in the protein-DNA binding reaction. Human bladder carcinoma ras oncogene promoter plus plasmid was obtained from Dr. Merlino, NIH. The human Harvey ras oncogene promoter DNA was 551 base pairs in length and was isolated by using Nae I restriction enzyme (FIG. 1). After the promoter DNA fragment was isolated, it was end labelled at the 5'-end with [gamma-32P]-ATP in the presence of polynucleotide kinase. Such purified and radiolabelled ras promoter DNA probe were then used in the mobility band shift assay.

Optimum concentrations of the end-labelled ras oncogene promoter were determined to be about 10,000 cpm per ng of DNA.

DNA Mobility Band Shift Assay and Gel

Further in accordance with this invention, binding reactions between serum factors from normal donors or from cancer patients and 32-P-labelled promoter DNA were performed in the buffer system described by Sen and Baltimore (Cell, 46:705-716 (1986)). This buffer system consists of 10 mM Tris (pH 7.5), 40 mM NaCl, 1 mM EDTA, 1 mM 2-mercaptoethanol and 4% glycerol. This buffer system shall be referred to as the "buffer system." End labelled 32-P-ras promoter DNA (about 10,000 cpm, 1-2 ng DNA, Maniatis, T., Fritsch, E. F., and Sambrook, J., *Molecular Cloning* (1982), several different concentrations of serum proteins and about 3 ug of polydeoxyinosinicpolydeoxycytidylic [poly-d(IC)] were incubated for 30 minutes on ice in a total reaction volume of 20 microliters. The poly-d(IC) was used as a nonspecific DNA to bind nonrelated serum factors. To eliminate nonrelated serum factors binding reactions were modified with respect to poly d(IC) concentrations and pre-incubation times before the addition of the radiolabelled DNA probe. In proceeding with the reaction between the serum factors, the poly-d(IC) and the radiolabelled ras promoter DNA probe, the free radiolabelled DNA and the complexed serum protein-DNA were further separated and identified on a 5% acrylamide gel. Such gels were then dried under vacuum, autoradiographed by exposure to x-ray film, developed after an appropriate incubation time and protein-DNA complexes were identified. The separated protein-DNA complexes migrated slower in the gel matrix and thus were readily differentiated from the free DNA. The amount of radiolabelled protein-DNA complex was then quantified by determining the amount of radioactivity specific to the complex as compared to the free radiolabelled DNA.

Optimum Preincubation Concentration of poly d(IC)

In accordance with yet another embodiment of this invention, several concentrations of poly d(IC) were used to determine the optimum concentration which would eliminate the maximum amount of nonspecific serum proteins and still allow the specific factors to bind to the radiolabelled ras promoter DNA in the mobility band shift assay. The nonspecific serum factors from the patient's or the normal donor's sera can be removed by preincubating serum with between 2.5 and 10 ug o poly d(IC), with the optimum concentration generally being about 7.5 ug of poly d(IC) in a total reaction volume of 20 microliters. Similarly, the pre-incubation time before the addition of the radiolabelled ras promoter DNA is between 10 and 60 minutes with the optimum time being about 30 minutes. Similarly, the reaction is performed at a temperature not exceeding 7° C. with a temperature of about 4° C. being optimum.

Optimum Concentration of Radiolabelled ras Promoter DNA Probe

In accordance with yet another embodiment of this invention, several concentrations of 32-P-labelled ras promoter DNA probe were added to the reaction admixture, incubated for about 30 minutes at a temperature of about 4° C. and then analyzed on a 5% acrylamide gel. The gels were further analyzed for the maximum amount of protein-DNA complex formed as a function of the concentration of the radiolabelled ras promoter DNA probe.

Increasing concentrations of radiolabelled ras promoter DNA probe of 5000 cpm/1 ng, 10,000 cpm/2ng, 15,000 cpm/3ng and 20,000 cpm/4ng were used and it was determined that the protein-DNA complex formation increased in the patient's serum samples as the radiolabelled ras promoter DNA probe concentrations increased. The protein-DNA complex of normal serum did not increase with the increased concentrations of radiolabelled DNA. This suggested that the DNA concentrations described supra were not in a limited amount in the reaction. Thus, if specific serum factors were present in the normal serum samples, under the conditions presented herein, binding between the serum factors and the radiolabelled DNA could have occurred.

Competition Experiments to Determine the Specificity of Binding Factors

In accordance with yet another embodiment of this invention, to determine if the interaction between the serum protein(s) and the radiolabelled ras promoter DNA is specific, a series of competition experiments were designed. After the patient's serum was pre-incubated with about 7.5 ug of poly d(IC), incubated for about 30 minutes at a temperature of about 4° C., specific or nonspecific competing DNA was added to the above admixture. The incubation of the above admixture was for about 10 minutes at a temperature of about 4° C. Specific DNA is defined as 50-100 fold excess of unlabelled ras promoter DNA and nonspecific DNA was defined as 100 fold excess PUC DNA or 1000 fold excess salmon sperm DNA (both the PUC and the salmon sperm DNA are nonspecific in nature and thus should not compete). When 50 or 100 fold excess unlabelled ras promoter DNA was included in the above admixtures, the amount of radiolabelled protein-DNA complex decreased accordingly. Similarly, no decrease in the amount of radiolabelled protein-DNA complex was observed when either 100 or 1000 fold excess of nonspecific DNA was added to the admixture.

Fractionation of Human Serum Factors on DEAE-Cellulose Columns

In accordance with yet another embodiment of this invention, before the human serum factors were used in the mobility band shift assay, they were fractionated on a DEAE-Cellulose column. The further processing of the serum factors prior to the mobility band shift assay allowed for nonspecific factors to be reduced to lower levels. The human serum was passed through a DEAE-Cellulose resin column which was equilibrated in the following buffer system: 25mM Hepes (pH 7.6), 40 mM KCl, 0.1 mM EDTA, 1 mM DTT, 10% glycerol containing 0.1 M NaCl. Under the above conditions, the nonspecific factors bind to the DEAE-Cellulose column thereby allowing the specific serum factors to be collected in the flow through fractions and to be further used in the mobility band shift assay.

Detection Systems for ras Oncogene Family Related Malignancies

The ras oncogene promoter DNA, when prepared in accordance with this invention, is suitable for use in a kit and assay system for the detection of serum proteins from patients with ras oncogene related malignancies. Such a kit may include, in addition to the labelled ras promoter DNA in a suitable container, a reactive positive control serum and a nonreactive negative control serum in suitable containers. Poly d(IC) would also be packaged in this kit. In accordance with the preferred embodiment, in addition to the reagents supplied, a detailed set of instructions would be provided in order to perform the mobility band shift assay, as well as optimizing for the pre-incubation concentration of poly d(IC), the amount of radiolabelled ras promoter DNA to add, the incubation times, etc.

First or primary antibodies generated against proteins which bind specifically to a region or regions of the ras oncogene promoter DNA, when prepared in accordance with this invention, are suitable for use in a kit and assay system for the detection of specific circulating antigens in biological samples from patients with ras oncogene related malignancies. Such a kit may include, in addition to the individual first or primary antibodies in suitable containers, one or more second or secondary antibodies specific for the first or primary antibodies in suitable containers, a labelled tag for identifying the second antibody in a suitable container and a positive and negative control antigen in suitable containers. In accordance with the preferred embodiment, in addition to the reagents supplied, a detailed set of instructions would be provided to direct the user in separating and identifying an antibody-protein complex. The methodology described to the user for identifying the antibody-antigen (protein) complex would be standard assays employed for the detection of these complexes (Western blot, immunodot blot, enzyme immunoassay or radioimmunoassay).

EXAMPLE 1

Figure 2:
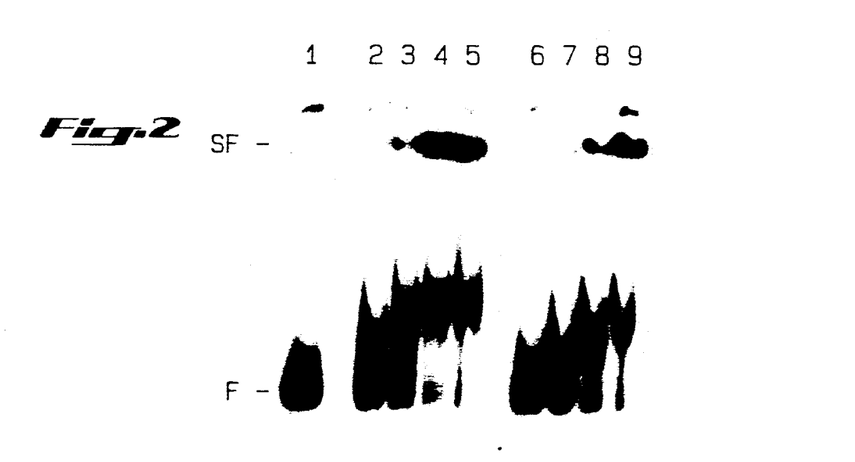
FIG. 2: Detection of protein-DNA complexes with tumor progression in serum from A/J mice injected with one million clonal neuroblastoma cells using the mobility band shift assay. Serum was drawn from mouse #1 and mouse #2 before cells were intraperitoneally injected (pretumor), one, two and three weeks after injection of cells. Lane 1, radiolabelled DNA without the addition of serum. Lanes 2-5, pretumor, week 1, week 2, week 3 from mouse #1. Lanes 6-9, pretumor, week 1, week 2, week 3 from mouse #2. "SF" indicates where the serum factors specific for the ras oncogene promoter DNA migrate; "F" indicates where the free radiolabelled DNA migrates.

Detection of Serum Factors Specific to ras Oncogene Promoter DNA in Mice Harboring Neuroblastoma Tumors Clonal cell lines established from C-1300 mouse neuroblastomas will form solid tumors within two to three weeks after injection into syngenic A/J strain of mice. The tumor and pretumor serum were incubated with radiolabelled Harvey ras oncogene promoter DNA and the specific protein-DNA complexes were then separated on an acrylamide gel. Proteins from pretumor serum did not bind to the radioactive ras promoter DNA. However, proteins from the tumor serum samples demonstrated high levels of specific binding to the promoter DNA. Of interest was the observed correlation between the amount of serum protein-DNA complexes and the size of the tumor. The level of ras promoter specific serum proteins increased with the tumor progression. The data presented in FIG. 2 demonstrates the occurrence of increasing amounts of protein-DNA complexes over a three week period, coincident with progression of the tumor growth. Also, in several mice, detectable levels of ras promoter specific serum factors (ten fold increase over pretumor levels) were observed before palpable tumor was observed. Through a series of competition experiments, the binding of mouse serum factors to ras promoter DNA was demonstrated to be highly specific.

EXAMPLE 2

Detection of Human Serum Factors Specific to ras Oncogene Promoter DNA in Normal Tumor-Free Control Donors Serum samples from ten normal tumor-free donors were passed through DEAE-Cellulose resin equilibrated with above-mentioned buffer plus 0.1M NaCl. A small amount of flow through material was pre-incubated with 7.5 ug of poly d(IC) for 30 minutes at 4° C., then incubated with radiolabelled ras oncogene promoter DNA for about 30 minutes at about 4° C. The reaction products were analyzed on a 5% acrylamide gel, which was further processed by drying under vacuum and exposing the dried gel to autoradiographic film prior to developing. The amount of complexed protein-radiolabelled DNA was further quantified by determining the amount of radioactivity in the protein-DNA complex relative to the amount of radioactivity in the free uncomplexed DNA.

Figure 3:
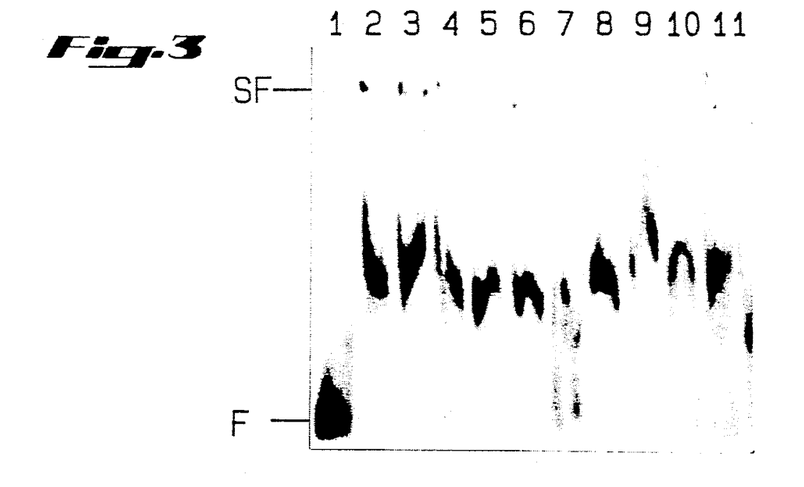
FIG. 3: Detection of protein-DNA complexes in serum from normal donors using the mobility band shift assay. Lane 1, radiolabelled DNA without the addition of serum; Lanes 2-11, 10 serum samples from normal donors.

As is observed in FIG. 3, the results of all ten normal tumor-free control donors indicated only basal levels of serum factors complexed to the ras oncogene promoter DNA. In three out of the ten normal donor samples, there was no detectable amount of protein-DNA interactive material observed.

EXAMPLE 3

Detection of Human Serum Factors Specific to ras Oncogene Promoter DNA in Patients with Colon Cancer Serum samples from ten patients with colon cancer were passed through DEAE-Cellulose resin equilibrated with above-mentioned buffer plus 0.1M NaCl. A small amount of flow through material was pre-incubated with 7.5 ug of poly d(IC) for 30 minutes at 4° C., then incubated with radiolabelled ras oncogene promoter DNA for about 30 minutes at about 4° C. The reaction products were analyzed on a 5% acrylamide gel which was further processed by drying under vacuum and exposing to autoradiographic film prior to developing. The amount of complexed protein-radiolabelled DNA was further quantified by determining the amount of radioactivity in the protein-DNA complex relative to the amount of free uncomplexed DNA.

Figure 4:
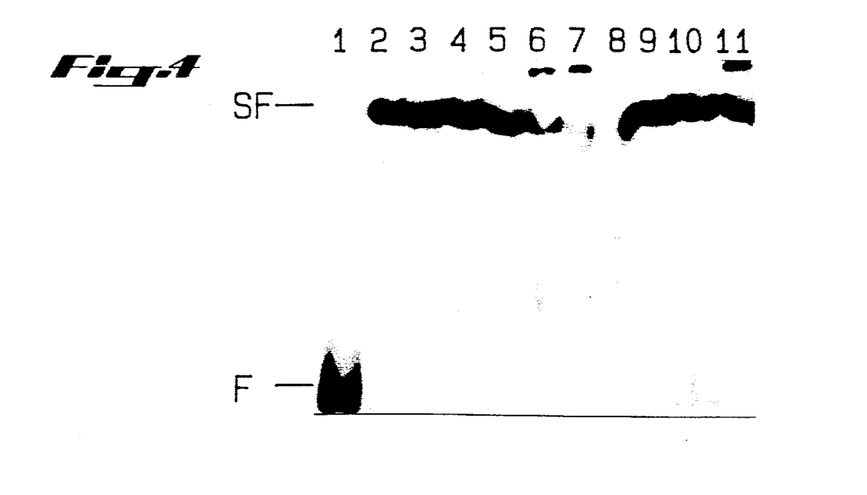
FIG. 4: Detection of protein-DNA complexes in serum from patients with colon cancer using the mobility band shift assay. Lane 1, radiolabelled DNA without the addition of serum; Lanes 2-11, 10 serum samples from patients with colon cancer.

The results from the ten patients with colon cancer presented in FIG. 4, demonstrated that nine out of the ten serum samples were positive for the presence of specific serum factors that interacted with the radiolabelled ras oncogene promoter DNA probe. The levels of serum factors specific for the ras oncogene promoter DNA probe ranged between 10 and 30 fold higher than the basal levels found in the sera from the normal control donors. The frequency of the presence of serum factors in patients with colon cancer was 90%. This method of detection was therefore positive for 90% of the colon serum samples.

EXAMPLE 4

Detection of Human Serum Factors Specific to ras Oncogene Promoter DNA in Patients with Prostate Cancer Serum samples from ten patients with prostate cancer were passed through DEAE-Cellulose resin equilibrated with above-mentioned buffer plus 0.1M NaCl. A small amount of the flow through material was pre-incubated with 7.5 ug poly d(IC) for 30 minutes at 4° C., then incubated with radiolabelled ras oncogene promoter DNA for about 30 minutes at about 4° C. The reaction products were analyzed on a 5% acrylamide gel and further processed and quantified as described above.

Figure 5:
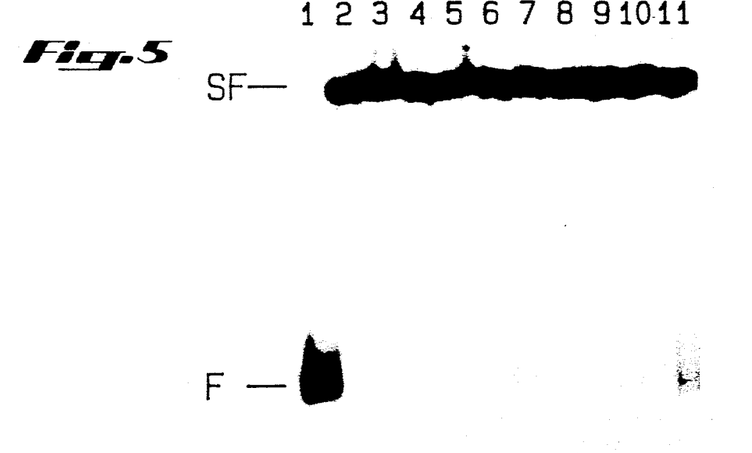
FIG. 5: Detection of protein-DNA complexes in serum from patients with prostate cancer using the mobility band shift assay. Lane 1, radiolabelled DNA without the addition of serum; Lanes 2-11, 10 serum samples from patients with prostate cancer.

The results from the ten patients with prostate cancer as seen in FIG. 5, demonstrated that all ten of the serum samples were positive for serum factors that specifically interacted with the ras oncogene promoter DNA. The levels of serum factors ranged between 20 and 35 fold higher than the amounts detected with the normal sera. The frequency of the presence of serum factors in patients with prostate cancer was 100%. This method of detection was therefore positive for 100% of the patients with prostate cancer.

EXAMPLE 5

Detection of Human Serum Factors Specific for the ras Oncogene Promoter DNA in Patients with Breast Cancer Serum samples from ten patients with breast cancer were passed through DEAE-Cellulose resin equilibrated and processed as described above. The mobility band shift assay was performed and the products were analyzed and quantified as described above.

Figure 6:
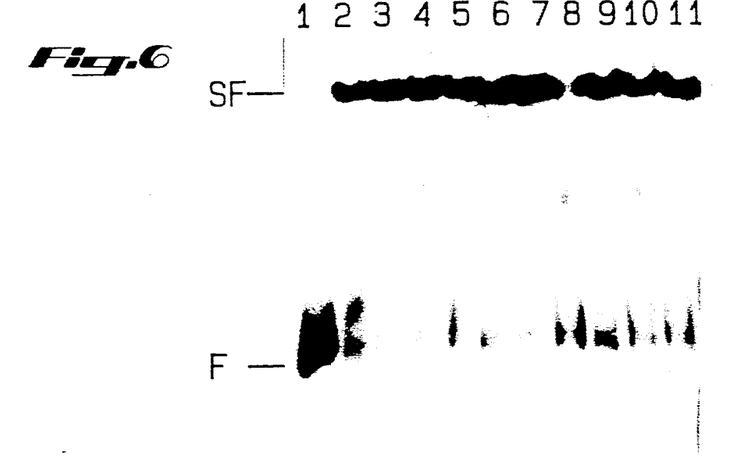
FIG. 6: Detection of protein-DNA complexes in serum from patients with breast cancer using the mobility band shift assay. Lane 1, radiolabelled DNA without the addition of serum; Lanes 2-11, 10 serum samples from patients with breast cancer.

The results from the ten patients with breast cancer as observed in FIG. 6, demonstrated that all ten of the serum samples were positive for serum factors that specifically interacted with the ras oncogene promoter DNA. The levels of serum factors ranged between 15 and 30 fold higher than the amounts detected with the normal sera. The frequency of the presence of serum factors in patients with breast cancer was 100%. This method of detection was therefore positive for 100% of the patients with breast cancer.

EXAMPLE 6

Detection of Human Serum Factors Specific for the ras Oncogene Promoter DNA in Patients with Melanoma Serum samples from ten patients with melanoma were processed, analyzed and quantified as described in the above-mentioned examples.

Figure 7:
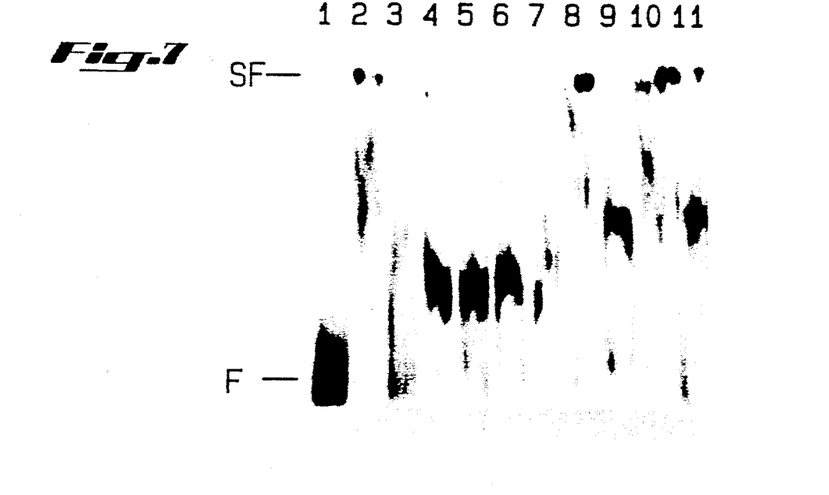
FIG. 7: Detection of protein-DNA complexes in serum from patients with melanoma using the mobility band shift assay. Lane 1, radiolabelled DNA without the addition of serum; Lanes 2-11, 10 serum samples from patients with melanoma.

The results from the ten patients with melanoma demonstrated that only four out of the ten patients were positive for serum factors that specifically interacted with the ras oncogene promoter DNA (FIG. 7). The levels of serum factors ranged between 10 and 15 fold higher than the amounts detected in the normal sera. The frequency of the presence of serum factors in patients with melanoma was 40%. Thus, this method of detection was positive for 40% of the patients with melanoma.

EXAMPLE 7

Characterization of the Serum Factors Specific for the ras Oncogene Promoter DNA In order to characterize the above-mentioned factors, serum from cancer patients was treated with 10 ug of trypsin for 20 minutes at 30° C. The mobility band shift assay was then performed on this pre-treated material. The results demonstrated that the trypsin treatment eliminated the specific interaction between the serum factors and the radiolabelled ras oncogene promoter DNA. These results demonstrate that serum factors which specifically bind to the ras promoter DNA are proteins. Heat treatment (55° C. for 20 minutes) did not eliminate the interaction between the serum factors and the ras promoter DNA, thus indicating that the specific serum factors are heat stable.

Figure 8:
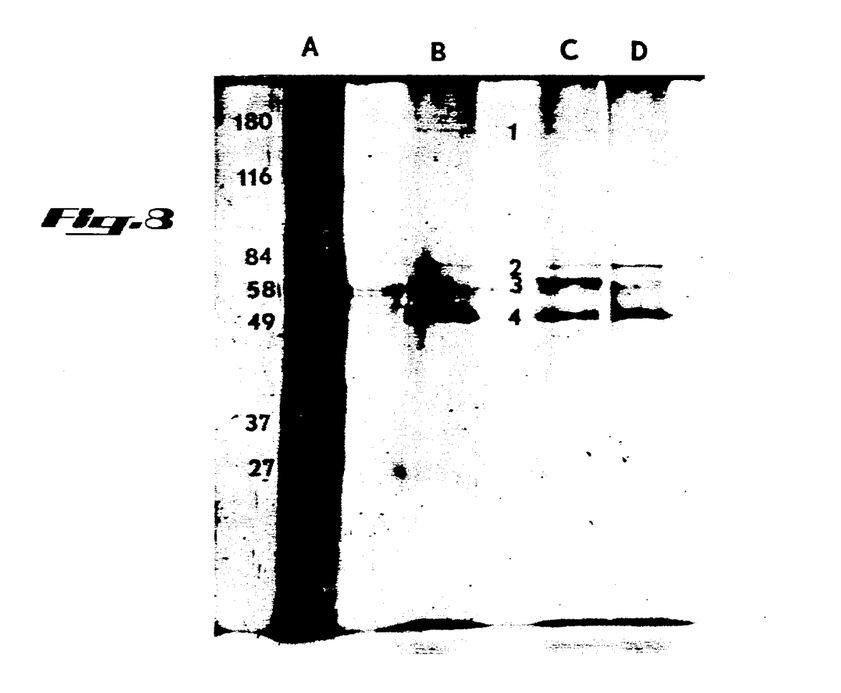
FIG. 8: Silver stained acrylamide gel analyses of protein-DNA complexes from a representative sample of prostate, breast and colon cancer. The molecular weights of the four observed proteins comprising the protein-DNA complex are indicated.

To determine the composition of the material which specifically interacts with the ras oncogene promoter DNA, the protein-DNA complex was further analyzed on an acrylamide gel. Using standard procedures familiar to those related to this area of the art, proteins were eluted from the protein-DNA complex, separated on an acrylamide gel, and visualized by silver stain. As observed in FIG. 8, four distinct and different proteins were observed and the approximate molecular weights of these proteins were about 170 Kd, 75 Kd, 70 Kd and 50 Kd.

While the compositions and methods of this invention have been described in terms of preferred embodiments, it will be apparent to those of skill in the art that various changes may be made in the composition, methods and in the steps or in the sequence of steps of the method described herein without departing from the concept and scope of the invention as defined by the following claims.

What is claimed is:

1. A method for detecting ras oncogene related malignancy in a human subject, comprising the steps of:
   a) collecting a test serum or plasma sample from a human subject;
   b) providing a control serum or plasma sample from a tumor free donor;
   c) incubating each of the control and test samples with a DNA having a sequence consisting essentially of a human ras oncogene promoter under conditions effective to promote specific binding interactions between protein factors in the samples and the DNA sequence;
   d) separating in each of the control and test samples a protein factor-DNA complex from free DNA; and
   e) comparing the amounts of protein factor-DNA complex of both the test and control samples, wherein if the test sample features an amount of about 10-fold or higher of a protein factor-DNA complex than the control sample, there is an indication of a ras oncogene related malignancy.

2. The method of claim 1, wherein the ras oncogene related malignancy is prostate cancer.

3. The method of claim 1, wherein the ras oncogene related malignancy is breast cancer.

4. The method of claim 1, wherein the ras oncogene related malignancy is colon cancer.

5. The method of claim 1, wherein a ras oncogene related malignancy is melanoma.

6. The method according to claim 1, wherein the step of detecting ras oncogene related malignancy includes the step of separating the factor-DNA complex from the reaction mixture by gel electrophoresis.

7. The DNA of claim 1, wherein the human ras oncogene promoter is derived from a family of genes consisting of either Harvey, Kirsten or neuroblastoma ras oncogene.

8. The method of claim 1, wherein the human ras oncogene promoter is a human Harvey ras oncogene promoter comprising a Nae 1-Nae 1 DNA fragment encompassing 551 base pairs of nucleotide sequences from 116–666.

9. The method of claim 1, wherein the DNA consists essentially of an entire DNA sequence specific for the coding of the human Harvey ras oncogene.

10. The method of claim 1, wherein the DNA consists essentially of the ras promoter and a DNA sequence specific for the coding of a heterologous eukaryotic or prokaryotic gene.

11. The method of claim 1, wherein the protein factor-DNA complex comprises 4 different proteins each ranging in molecular weight from about 200 Kd to about 50 Kd.

12. A method for diagnosing ras oncogene related malignancy in a human subject, the method comprising:
detecting in a serum or plasma sample from the human subject, proteins complexed with a DNA having a sequence consisting essentially of a human ras oncogene promoter, the proteins having a range of molecular weights from about 200 Kd to about 50 Kd according to their relative electrophoretic migration rate through a gel matrix, and such complexes being an indicator of ras oncogene related malignancy.

13. A method according to claim 12, wherein the protein is trypsin sensitive and heat stable.

14. A method according to claim 12, wherein the labelled DNA comprises the human Harvey ras promoter oncogene.

15. A diagnostic kit for detecting an oncogene related malignancy in a human subject which comprises multiple containers wherein the following is included in separate containers: a human ras oncogene promoter DNA sequence, a positive control comprised of a protein which specifically binds to the ras oncogene promoter and a negative control comprised of a protein which does not bind to the promoter; the kit includes instructions which describe the separation and identification of a protein-DNA complex.

16. The diagnostic kit of claim 15, wherein the ras oncogene promoter DNA comprises the promoter region alone, the promoter region added to a DNA sequence specific for the coding of an oncogene, or the promoter region added to a DNA sequence specific for coding any other eukaryotic or prokaryotic gene.

* * * * *